(12) United States Patent
Nakamura

(10) Patent No.: US 6,177,681 B1
(45) Date of Patent: Jan. 23, 2001

(54) APPARATUS METHOD FOR TESTING OPENING STATE FOR HOLE IN SEMICONDUCTOR DEVICE

(75) Inventor: Toyokazu Nakamura, Tokyo (JP)

(73) Assignee: NEC Corporation, Tokyo (JP)

( * ) Notice: Under 35 U.S.C. 154(b), the term of this patent shall be extended for 0 days.

(21) Appl. No.: 09/236,332

(22) Filed: Jan. 25, 1999

(30) Foreign Application Priority Data

Jan. 27, 1998 (JP) .................................................. 10-029161

(51) Int. Cl.⁷ .................................................. G01N 21/86
(52) U.S. Cl. .................................... 250/559.42; 250/341.4
(58) Field of Search ........................ 250/559.42, 559.43, 250/559.45, 341.4, 343, 306, 307; 356/237.6, 237.1, 73

(56) References Cited

U.S. PATENT DOCUMENTS 5,612,539 * 3/1997 Hoshi et al. ...................... 250/341.4

FOREIGN PATENT DOCUMENTS 3-161949 7/1991 (JP) .
7-83841 3/1995 (JP) .

OTHER PUBLICATIONS

Process Technology for Devices, "Semiconductor World", Journal Corporation, vol. 16, No. 9, Jul. 1997, pp. 76–79.
H. Todokoro et al., "Observation of Deep Holes using a New Technique", Japan Society for Promotion of Science, Application to Charged Particle Beam, 132–th Committee, 121–th Research Conference, Document, pp. 156–161, Dec. 1998.

T. Koizumi et al., "Cyclotron SEM", Japan Society for Promotion of Science, Application to Charged Particle Beam, 132–th Committee, 113–th Research Conference, Document, pp. 1550160, Dec. 1998.

T. Ohtaka et al., "Deep Hole Observation Method by Surface Field Control FCM Method)", Japan Society for Promotion of Science, Application to Charged Particle Beam, 132–th Committee, 117–th Research Conference, Document, pp. 165–169, Dec. 1998.

* cited by examiner

*Primary Examiner*—Que T. Le
(74) *Attorney, Agent, or Firm*—Sughrue, Mion, Zinn, Macpeak & Seas, PLLC

(57) ABSTRACT

A testing apparatus for an opening state of a hole in a semiconductor device includes a laser light radiating system. The semiconductor device has the conductive layer and the insulating layer formed on the conductive layer, and the hole is formed in the insulating layer at aim to reach the conductive layer. The laser light radiating system radiates to a hole, a laser light having a wave length determined based on a work function of a material of a conductive layer and a work function of a material of an insulating layer. A detector detects photoelectrons emitted through a portion of the hole to which the laser light is irradiated. A charge supplementing mechanism supplies electrons to the conductive layer.

26 Claims, 7 Drawing Sheets

APPARATUS METHOD FOR TESTING OPENING STATE FOR HOLE IN SEMICONDUCTOR DEVICE

BACKGROUND OF THE INVENTION

1. Field of the Invention

The present invention relates to a semiconductor device manufacturing method, and more particularly, to a testing technique of the opening state of a hole, such as a via-hole and a contact hole, which is formed in a process of manufacturing a semiconductor device.

2. Description of the Related Art

Conventionally, a scanning electron microscope (SEM) is used to test a contact hole and a via-hole formed in a process of manufacturing a semiconductor device. As such a technical field, for example, a technique is well known which is described in "Semiconductor World" (issued by Press Journal Corporation, Vol.16, No.9, pages 76–79, July 1997).

In the test method using the SEM, a primary electron beam is scanned while being irradiated to the surface of a semiconductor substrate. Then, secondary electrons generated from the bottom surface of a hole formed in a semiconductor substrate are detected by a secondary electron detector. It is determined based on the detected result by the secondary electron detector whether or not the hole is uniformly opened up to the bottom thereof by etching.

When the hole is perfectly opened, namely, when an insulating film is perfectly removed, the secondary electrons are generated from a lower conductive layer of the bottom of the perfectly opened hole. The generated secondary electrons pass through the hole and then are detected by the secondary electron detector. On the other hand, when an imperfectly opened hole is formed, the secondary electrons are generated from an intermediate insulating film as the bottom of the imperfectly opened hole. The generated secondary electrons pass through the imperfectly opened hole and then are detected by the secondary electron detector. In other words, when the intermediate insulating film is not perfectly removed and remains to cover the lower conductive layer, the secondary electrons generated from the surface of the insulating film at the bottom of the hole pass through the imperfectly opened hole and then are detected by the secondary electron detector.

In this way, the principle of detecting the above-mentioned perfect opening utilizes a fact that an amount of secondary electrons arriving at the secondary electron detector is different between when the perfectly opened hole is formed and when the imperfectly opened hole is formed.

It could be considered that this difference between the amounts of detected secondary electrons depends on a difference between charge accumulating capabilities in the bottom surfaces of the holes rather than a difference between materials of the bottom surfaces of the holes. That is, in the case of the perfectly opened hole, the irradiated primary electron beam arrives at the lower conductive layer and the electrons are grounded through the lower conductive layer. Thus, the electrons are not accumulated. However, in the case of the imperfectly opened hole, the electrons cannot arrive at the lower conductive layer. Hence, the electrons are accumulated on the surface of the intermediate insulating film of the bottom surface of the hole.

Associated with the development of multi-layer technique from the late of 1990's, in a contact hole and a via-hole, the aspect ratio has become higher. At the same time, the hole diameter has become smaller. For these reasons, it is difficult to observe the bottom of the hole by using the scanning electron beam. The opening in the range of an aspect ratio from 2 to 3 can be observed by using the scanning electron beam. However, in a case of an aspect ratio of a value larger than the above-mentioned value, the opening cannot be observed by using the scanning electron beam. Thus, it is difficult to detect a defective opening.

For the purpose of observation of the bottom of a hole having the high aspect ratio, a research result is described in "Observation of Deep Holes using a New Technique" from Japan Society for Promotion of Science, (Application to Charged Particle Beam, 132-th Committee, 121-th Research Conference, Document, pp. 156–161). Also, there are "Cyclotron SEM" from the same Committee, (113-th Research Conference, Document, pp. 155–160), and "Deep Hole Observation Method by Surface Field Control (FCM Method)" from the same Committee, (117-th Research Conference, Document, pp. 165–169). In addition, there is known "SEMSpec" from KLA Corporation which uses an electron beam current approximately 1000 times larger than that of the conventional SEM. Thus, it has become possible to test the open state.

However, if the SEM is used, the measurement range is generally narrow. This results in a problem that an test throughput is low.

In addition, the SEM method has problems described below. That is, the apparatus itself is large in size and expensive. Further, although there is a need of a contrast test under a condition that resist is coated, the test cannot be carried out because the resist is charged up by electrons.

Further, it cannot be determined in the opening test of a via-hole whether or not a barrier layer such as a TiN layer is kept in good state. This is because the contrast due to a difference between materials such as aluminum and TiN is small in an SEM image.

Further, if the bottom of a hole is covered by only an extremely thin natural oxide film, the primary electron passes through the thin oxide film in the SEM method. This leads to the small difference between a perfectly opened hole and an imperfectly opened hole in charge accumulating capability. As a result, it becomes difficult to detect the imperfectly opened hole.

Under such a situation, another contact hole testing method is disclosed in Japanese Laid Open Patent Application (JP-A-Heisei 7-83841). In the reference (JP-A-Heisei 7-83841), an ultraviolet laser beam generated from an ultraviolet laser beam source 101 is irradiated to a test target 107 using a rotary multi-surface mirror 105 and a scan lens 106. An ultraviolet light reflected from the test target 107 is received by a reflected light optical system composed of the scan lens 106, the rotary multi-surface mirror 105 and a beam splitter 104. The received reflected ultraviolet beam is focused by a lens 108 and a pin-hole 109 such that an image corresponding to a region for a via-hole of the test target 107 is imaged on a photomultiplier 110. As a result, a reflected ultraviolet detection signal is outputted.

Also, another contact hole testing method is disclosed in Japanese Laid Open Patent Application (JP-A-Heisei 3-161949). In this method, a laser light having an energy lower than a work function of an upper layer is irradiated to the contact hole. Then, it is determined whether or not photoelectrons are detected from the contact hole. As a result, the open state of the contact is tested on the basis of the determination.

However, if this method is applied to the test of many contact holes, a silicon substrate as a lower layer is gradually and positively charged by the emission of the photoelectrons. This causes a problem that the photoelectrons are prevented from being emitted out of the wafer substrate. For this reason, it becomes difficult to test the many contact holes.

Also, there is a case that a lower aluminum wiring layer is insulated from a silicon substrate by another intermediate insulating film. In such a case, if the above-mentioned opening testing method is applied to the via-holes between wiring layers, the wiring layer is easily and positively charged up, because the capacity of the wiring layer is small. For this reason, it is difficult to continuously test the many contact holes.

SUMMARY OF THE INVENTION

The present invention is accomplished to solve the above-mentioned problems. Therefore, an object of the present invention is to provide a method for testing an opening state of a hole in a process of manufacturing a semiconductor device and an apparatus for the same.

Another object of the present invention is to provide a method for testing an opening state of many holes, each of which has a large aspect ratio and a small diameter, and an apparatus for the same.

In order to achieve an aspect of the present invention, a testing apparatus for an opening state of a hole in a semiconductor device includes a laser light radiating system. The semiconductor device has the conductive layer and the insulating layer formed on the conductive layer, and the hole is formed in the insulating layer at aim to reach the conductive layer. The laser light radiating system irradiates to a hole, a laser light having a wave length determined based on a work function of a material of a conductive layer and a work function of a material of an insulating layer. A detector detects photoelectrons emitted through a portion of the hole to which the laser light is irradiated. A charge supplementing mechanism supplies electrons to the conductive layer.

It is desirable that the wave length of the laser light is a wave length corresponding to an energy in a range in which an outer photo-electric effect is performed to the conductive layer but the outer photo-electric effect is not performed to the insulating layer. Also, the laser light is focused on and irradiated to a bottom surface of the hole. At that time, it is determined based on the detecting result by the detector whether or not the hole is opened to reach the conductive layer.

The charge supplementing mechanism may include an electron beam source for sending the electrons to the conductive layer. Instead, the charge supplementing mechanism may be connection of the conductive layer of the semiconductor device to the ground to send the electrons to the conductive layer. In this case, the testing apparatus may further include a controller for controlling the laser light radiating system and the electron beam source such that the radiation of the laser light and the electron supplement to the conductive layer by the electron beam source are alternately carried out.

The semiconductor device may have a plurality of the holes and a focused beam diameter of the laser light is larger than a diameter of the hole.

The laser light radiating system has an optically scanning system for scanning the laser light in a two-dimension direction such that the laser light is sequentially irradiated to the plurality of holes. Instead, the laser light radiating system may include an optically scanning system for scanning the laser light in a one-dimension direction such that the laser light is sequentially irradiated to a row of the plurality of holes, and a driver for scanning the semiconductor device in a direction orthogonal to a scanning direction of the laser light, in response to the scan of the laser light. Otherwise, the testing apparatus may further include a driver for scanning the semiconductor device in a two-dimension direction such that the laser light is sequentially irradiated to the plurality of holes.

The detector may be a light electron detector, or an ammeter connected between the conductive layer and the ground.

In addition, the testing apparatus may further include a display, and a display controller for controlling the display such that the detecting result by the detector is displayed on the display with respect to a relative position of the semiconductor device and the laser light. In this case, the display controller desirably controls the display such that the detecting result by the detector for each of the plurality of holes in the semiconductor device is displayed on the display as a two-dimension contrast image having a brightness distribution proportional to the detection result.

In order to achieve another aspect of the present invention, a method of testing an opening state of a hole in a semiconductor device, includes the steps of:

radiating to one of a plurality of holes, a laser light pulse having a wave length determined based on a work function of a material of a conductive layer and a work function of a material of an insulating layer, wherein the semiconductor device has the conductive layer and the insulating layer formed on the conductive layer and the plurality of holes are formed in the insulating layer at aim to reach the conductive layer;

detecting that photoelectrons are emitted through the hole in response to the laser light; and supplementing electrons to the conductive layer after the laser light pulse is irradiated.

DESCRIPTION OF THE PREFERRED EMBODIMENTS

Figure 1:
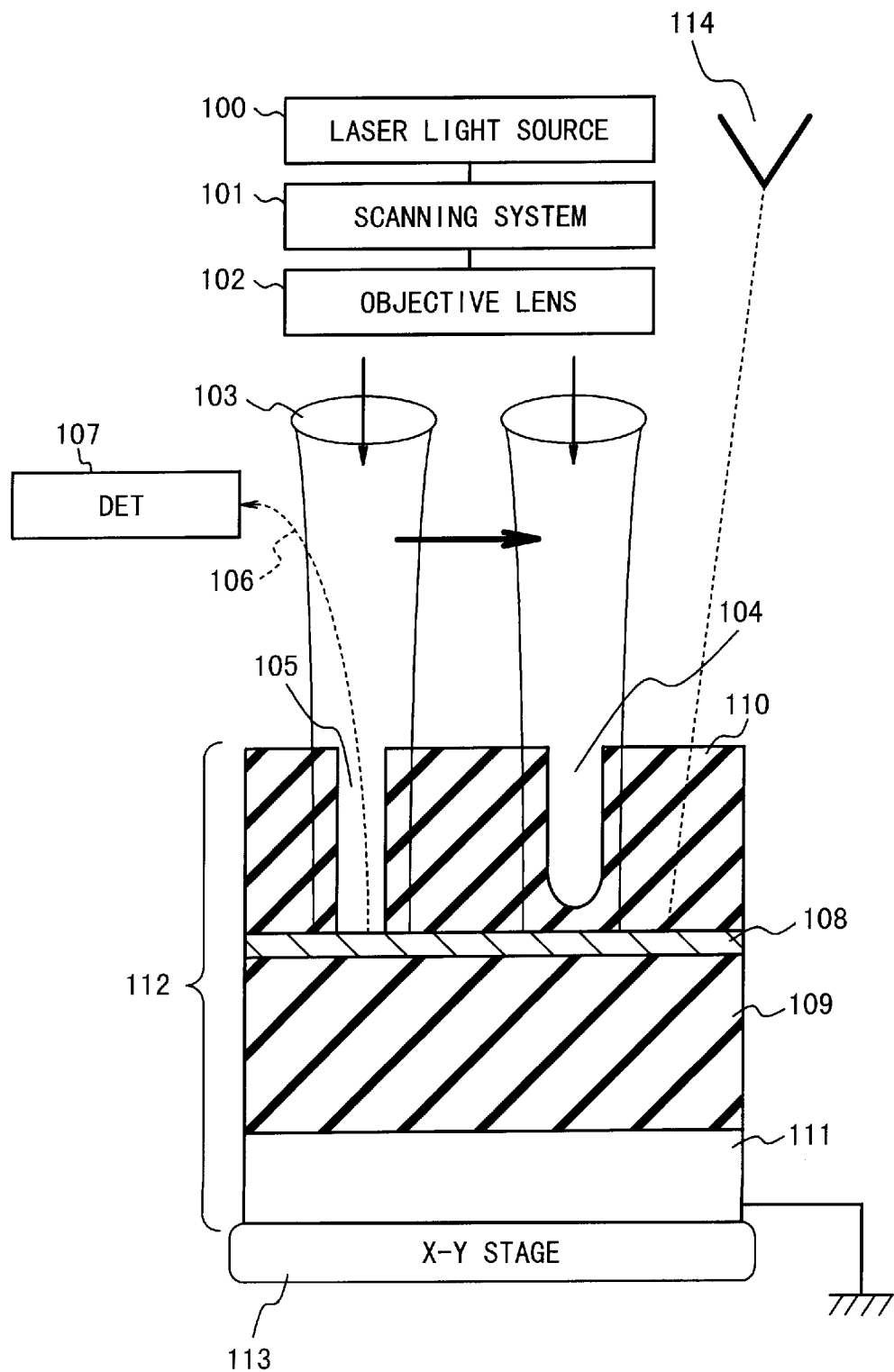
FIG. 1 is a conceptual diagram illustrating the present invention.

An apparatus for testing an opening state of a hole in a semiconductor device of the present invention will be described in detail below with reference to the attached drawings.

At first, the principle of the apparatus for testing the opening state of a hole in the semiconductor device of the present invention will be described.

In the testing apparatus of the present invention, an amount of photoelectrons emitted from a surface of a lower layer by an outer photo-electric effect is measured, when a laser light is collected on the surface of the lower layer positioned to form the bottom of the hole. At this time, charges are separately supplied or supplemented to the lower layer.

If there is not an intermediate insulating film, an natural oxide film, and foreign things on the lower layer surface as the bottom surface of the hole, photoelectrons are relatively easily passed through the hole and then detected by a photoelectron detector disposed within a vacuum chamber. On the other hand, if there is the intermediate insulating film, the natural oxide film, or the foreign things on the lower layer surface to cover the lower layer, the photoelectrons generated within the covered wiring layer cannot contribute to the photoelectron measurement using the photoelectron detector. This is because the photoelectrons must penetrate the intermediate insulating film or the natural oxide film on the surface of the wiring layer.

In this way, the laser light is irradiated to the bottom surface of the hole and then an amount of generated photoelectrons is measured. Accordingly, it is possible to test the opening state of the hole, especially, the electrical contact performance of the bottom surface. In particular, if the energy of the laser light is set to be lower than the work function of the intermediate insulating film or the natural oxide film, the photoelectrons generated on the surface of the lower layer cannot penetrate the intermediate insulating film. Thus, the photoelectrons do not contribute to the photoelectron measurement by the photoelectron detector. As a result, there is a large difference between when the laser light is irradiated to the perfectly opened hole and when the laser light is irradiated to the imperfectly opened hole in an amount of photoelectrons. Also, it is desirable that the charge supply to the lower layer is performed to supplement electrons loss due to the emission of the photoelectrons.

When the laser light is scanned in X and Y directions on the surface of the wafer, while being kept substantially vertical to the surface of the wafer, the two-dimensional mapping of the detected amount of the photoelectrons can be obtained. In this case, if respective positions in the X and Y directions are mapped so as to have a brightness proportional to the detected amount of photoelectrons, the perfectly opened hole is represented as a bright point, and the imperfectly opened hole is represented as a dark point. This easily allows the imperfectly opened hole to be detected.

If it is intended to detect the imperfectly opened hole as mentioned above, it is not always necessary that the laser light is collected to have a light diameter smaller than the hole. It is enough that the respective holes can be separated and identified. Thus, when the holes are formed in the form of matrix, it is enough that the collected light diameter of the laser light is less than an interval between the holes. In this case, the collected light diameter of the laser light may be considerably large. Therefore, the time which is required to scan the laser light in the X and Y directions may be short. As a result, an extreme reduction of the test time can be realized.

Conventionally, when the testing method is performed to a hole, the electron beam is irradiated by the SEM, and the situation of the bottom of the hole is detected, as mentioned above. The secondary electrons generated on the bottom surface by the electron beam must pass through the hole and then jump from the surface of the wafer into the chamber. In this case, however, it could be considered that the traveling directions of the secondary electrons generated on the bottom surface of the lower layer are not only a vertical direction to the bottom surface. Hence, as the aspect ratio of the hole becomes larger, the secondary electrons collide with the side of the hole to be scattered and absorbed. The reason why the directions at the emission of the secondary electrons are distributed may be that there is an isotropical thermal factor with regard to the generation of the secondary electrons. Thus, the amount of secondary electrons that pass through the hole and are detected by the photoelectron detector is reduced. As a result, as the aspect ratio of the hole increases, it becomes more difficult to carry out the hole test by the SEM.

On the other hand, when the laser light is irradiated to the metal surface such as a wiring layer, the photoelectrons are generated by the photo-electric effect in a quantum theory process known as Fermi's golden level. That is, it is presumed that there are many components which are not parallel to the direction of the laser light beam, in the traveling directions of the photoelectrons. However, it could be presumed that the generated photoelectrons are aligned in phase and travelling direction by elastic collision to have the strongly coherent characteristic. Hence, when the laser light beam is irradiated substantially vertically to the surface of the wafer, the photoelectrons are generated and emitted without being captured by the side of the hole. Thus, it could be considered that many photoelectrons pass through the hole.

The reason why the photoelectrons can be effectively detected would be that the travel directions at which the above-mentioned photoelectrons are generated are biased to the vertical direction. Thus, the hole can be tested using the photoelectrons having information of the bottom of the hole having a high aspect ratio.

As mentioned above, the opened state of the hole can be tested by measuring the photoelectrons jumping up from the hole. As the laser lights are irradiated to the perfectly opened hole so that the photoelectrons are emitted, the negative charges are gradually removed from the lower layer. Thus, if the lower layer is not connected through the silicon substrate to the ground, the lower layer is charged up gradually and positively. When the charge amount reaches a certain value, the emission of the photoelectrons is suppressed. For this reason, if the lower layer is not connected to the ground, it is necessary to complete the measurement before the charging advances. Also, it is necessary to newly irradiate an electron beam to supplement the charges to the lower layer, or devise natural relaxation in air.

As mentioned above, if the wiring layer can be connected to the ground, a current flows to supplement for the charge loss due to the emission of the photoelectrons. The imperfectly opened hole can be detected even by measuring and mapping this current.

FIG. 1 shows the concept of a testing apparatus of an opening state of a hole in the present invention.

Referring to FIG. 1, the semiconductor device is placed on an XY stage 113. In the semiconductor device, a first intermediate insulating film 109 in which a first wiring layer (not shown) is formed, a second wiring layer 108 and a second intermediate insulating film 110 are formed in this order on a silicon substrate 111. A perfectly opened hole 105 and an imperfectly opened hole 104 are formed in the second intermediate insulating film 110 by an etching process.

The second wiring layer 108 as a lower layer to form the bottom of the opened hole is not connected to the ground by the first intermediate insulating film 109. Thus, the charge supplement is performed to the second wiring layer 108 by the electron beam irradiated by a charge supplement electron beam source 114.

A wave length of a laser light from a source 100 is shorter than a wave length corresponding to the work function of the conductive material of the second wiring layer 108. For example, if the second wiring layer 108 is made of aluminum, the wave length of the laser light from the source 100 is shorter than 292 nm corresponding to the aluminum work function of 4.25 eV.

If the second intermediate insulating film 110 is formed of $SiO_2$, a value corresponding to the work function of $SiO_2$ is a value in which the silicon oxide chemical shift amount of 4 eV is added to the Si work function of 4.8 eV, namely, 8.8 eV. Thus, it is sufficient that the energy of the laser light from the laser light source 100 is less than this energy of 8.8 eV. The light of 8.8 eV belongs to the region of an X-ray, and an optical energy of a ultraviolet laser is naturally lower than the above-mentioned energy. Hence, the utilization of the ultraviolet laser as the laser light source 100 meets the object of the present invention.

However, in order that the photoelectrons pass through the hole and then arrives at a photoelectron detector 107, it is necessary that the photoelectron has a certain kinetic energy. Thus, it is necessary to provide the kinetic energy equal to or greater than the energy of the secondary electron in the SEM. Hence, it is necessary that the laser light source 100 irradiates the laser light having an energy larger than the above-mentioned work function by a value from several tens of mili-electron-volts to several hundreds of mili-electron-volts.

For this purpose, a laser light source emitting a proper ultraviolet laser light is selected. For example, since an XeBr excimer laser has the oscillation wave length of 275 nm, it is suitable for the laser light source 100 of the present invention. The laser light irradiated by the laser light source 100 is scanned on the surface of the wafer by a laser light scanning system 101, and further focused on the bottom surface of the hole by an objective lens 102.

Photoelectrons 106 can be effectively measured by the photoelectron detector 107 when a laser light 103 is collected on a bottom surface of the perfectly opened hole 105. Even if the laser light is scanned in a state that the wafer is fixed, or even if the wafer is scanned in a state that the position of the laser light is fixed, the photoelectrons are scarcely detected when the hole is the imperfectly opened hole 104. Thus, the imperfectly opened hole 104 can be detected.

In order to test the many holes as mentioned above, it is necessary to supplement the charge to the lower wiring layer 108. For example, when the test for the opening state of the hole is intermittently carried out from a hole to another hole by using a laser pulse, an electron beam pulse is irradiated from the charge supplement electron beam source 114 through the second intermediate insulating film 110 to the second wiring layer 108, so that the charge supplement is carried out. Thus, the acceleration voltage of the electron beam to be irradiated is adjusted such that the beam electrons can pass through the second intermediate insulating film 110.

Next, a testing apparatus for an opening state of a hole according to a first embodiment of the present invention will be described below.

Figure 2:
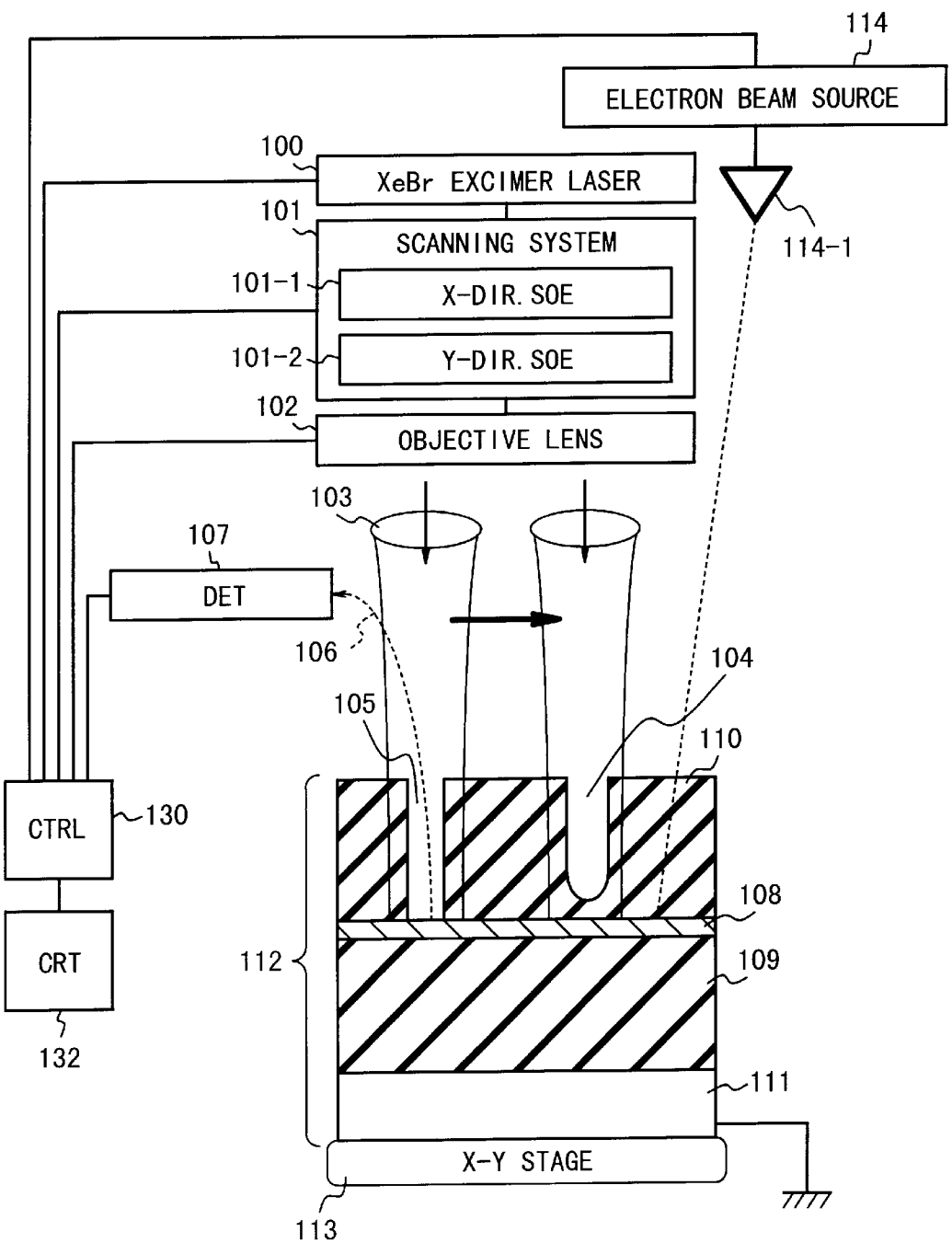
FIG. 2 is a diagram illustrating a testing apparatus for the opening state of a hole according to a first embodiment of the present invention.

FIG. 2 shows an example in which the testing apparatus in the first embodiment carries out a contact test of a hole referred to as a via-hole. Referring to FIG. 2, the testing apparatus is provided with an excitation laser light source (XeBr excimer laser) 100, a laser light scanning system 101, an objective lens 102, a photoelectron detector 107, an XY stage 113, a charge supplement electron beam source 114 having an electron gun 114-1, a controller 130 for controlling the testing apparatus as a whole and a display 132.

The semiconductor device or wafer is placed on the XY stage 113. In the semiconductor device, a first intermediate insulating film 109 in which a first wiring layer (not shown) is formed, a second wiring layer 108 and a second intermediate insulating film 110 are formed in this order on a silicon substrate 111. A perfectly opened hole 105 and an imperfectly opened hole 104 are formed in the second intermediate insulating film 110 by the etching process.

The XeBr excimer laser is used as the excitation laser light source 100. The light emission of the laser light is controlled by the controller 130. The XeBr excimer laser carries out a pulse oscillation with the wave length of 275 nm. When this wave length is used, the photoelectrons are emitted by the outer photo-electric effect, when the second wiring layer 108 as the lower layer is made of aluminum. However, when the second intermediate insulating film 110 is made of a $SiO_2$ film and further remains on the bottom surface of the hole, the photoelectrons cannot penetrate the second intermediate insulating film 110. This is because the second intermediate insulating film 110 has a larger work function.

The laser light scanning system 101 for scanning the laser light is composed of an X-direction scanning optical element (SOE) 101-1 and a Y-direction scanning optical element (SOE) 101-2. The optical elements 101-1 and 101-2 scan the laser light emitted from the XeBr excimer laser into an X-direction and a Y-direction under the control of the controller 130. A rotating polygon mirror as the laser light scanning system 101 may be used to scan the laser light. However, in this embodiment, an acoustical optical element superior in operation speed is used to scan the laser light in the X-direction and the Y-direction.

The objective lens 102 collects the laser light scanned by the laser light scanning system 101 on the bottom of the opened hole, i.e., on the surface of the second wiring layer 108, under the control of the controller 130. A lens belonging to a telecentric system is used as the objective lens 102. When the laser light is scanned, an optical axis of a laser light to be irradiated is adjusted so as to be always substantially vertical to the surface of the wafer. The optimization of the optical system enables a spot diameter of the laser light beam to be limited to 0.3 microns.

The charge supplement electron beam source 114 emits an electron beam from the electron gun 114-1 in accordance with the control of the controller 130. The electrons in the emitted electron beam are sent to the second wiring layer 108. While a probe test is performed to the respective holes by using the pulsed laser light, the electron beam pulse is irradiated from the charge supplement electron beam source 114 to the lower wiring layer to thereby carry out the charge supplement. That is, after the irradiation of the laser light pulse, the electron beam pulse is applied.

The photoelectron detector 107 detects the photoelectrons 106 to outputs the detected result to the controller 130, when the laser light 103 is irradiated to the semiconductor device. The controller 130 outputs to the display 132 the result detected by the photoelectron detector 107, in synchronous with the control in the X-direction and the Y-direction of the laser light scanning system 101. Accordingly, the detected result is displayed on the display 132 in the form of matrix.

Next, a method for testing an opening state of a hole will be described below.

As a sample, a semiconductor device is used which is formed on an 8-inch wafer having via-holes of a 64M-bit DRAM. The diameter of the via-hole is 0.6 microns, an interval between the via-holes is 1.2 microns and the aspect ratio is 5.

The bottom of the via-hole of this sample cannot be observed even if the conventional SEM is used. In this case, presence or absence of a film remaining inside the via-hole can be observed as a contrast of an SEM image, if the SEM is used in which an electron beam current is approximately 1000 times larger than that of the conventional SEM. However, unless the SEM is set to have a high magnification, the bottom of the via-hole cannot be observed. That is, the measurement field is narrow so that it takes a long time to test the whole wafer.

On the other hand, as mentioned above, the spot diameter of the laser light 103 used in this embodiment is 0.3 microns and four times larger than that of the electron beam. Thus, the measurement field can be made wider. The scanning speed is determined based on an interval between the spots generated by the laser light. It is necessary that the spot interval is set to be shorter than that between the via-holes 104 and 105. In this embodiment, the interval between the spots is 80% of the arrangement interval between the via-holes. The laser light is scanned in the two directions of X and Y by the laser light scanning system 101 in order to scan within the measurement field. A test wafer 112 itself is moved in order to move the measurement field.

After the above-mentioned settings are carried out, the photoelectrons emitted from the bottom surface of the via-hole are detected by use of the photoelectron detector 107 mounted within a vacuum chamber. The output of the photoelectron detector 107 is displayed on the display (CRT) 132 at a timing synchronous with the scanning of the laser light such that an operator can monitor the hole. As a result, the presence or absence of the remaining film composed of the second intermediate insulating film 110 in the via-hole can be observed.

When the via-hole of this sample is tested as mentioned above, the test can be carried out times faster than the SEM using the electron beam with a large current.

Next, a testing apparatus for an opening state of a hole according to a second embodiment of the present invention will be described below with reference to FIG. 3.

Figure 3:
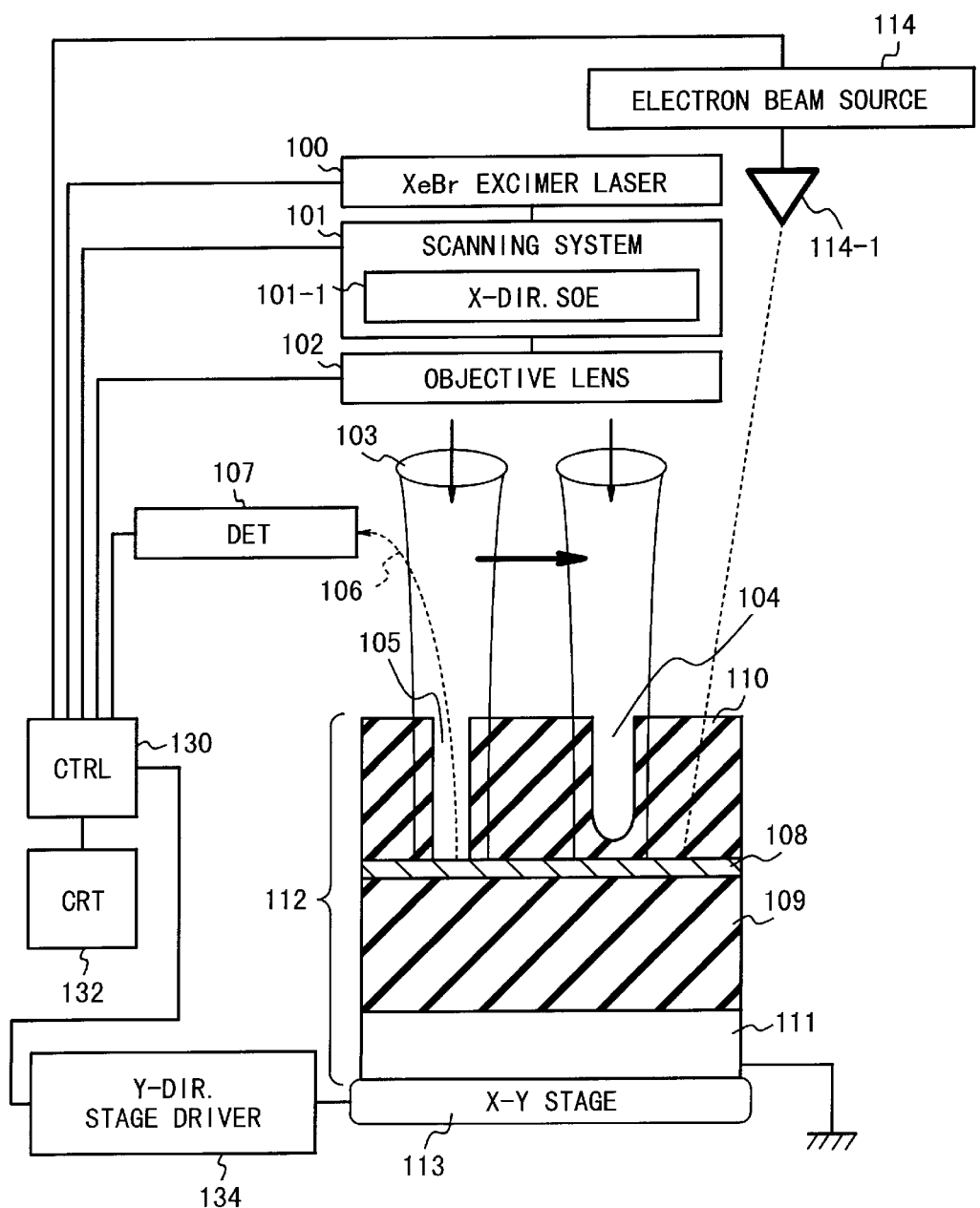
FIG. 3 is a diagram illustrating a testing apparatus for the opening state of a hole according to a second embodiment of the present invention.

The second embodiment is different from the first embodiment in that only an acoustical optical element (SOE) 101-1 for an X-direction scan is used in a laser light scanning system 101 shown in FIG. 3. In this case, the laser light is scanned only in a one-dimension of the X-direction by the laser light scanning system 101.

In the scanning into a Y-direction, an XY stage 113 on which a test wafer 112 is placed is scanned in the Y-direction by a Y-direction stage driver 134, under the control of the controller 130.

In the second embodiment, the laser light scanning system 101 is simple as compared with the first embodiment. Moreover, the tested hole image is obtained as a series of spot images, unlike an image composed of small spots in a matrix manner as in the first embodiment. Thus, the method for processing an image different from that of the first embodiment is applied to the series of spot images. As a result, the test result similar to that of the first embodiment is obtained, and the test speed is identical to that of the first embodiment.

Figure 4:
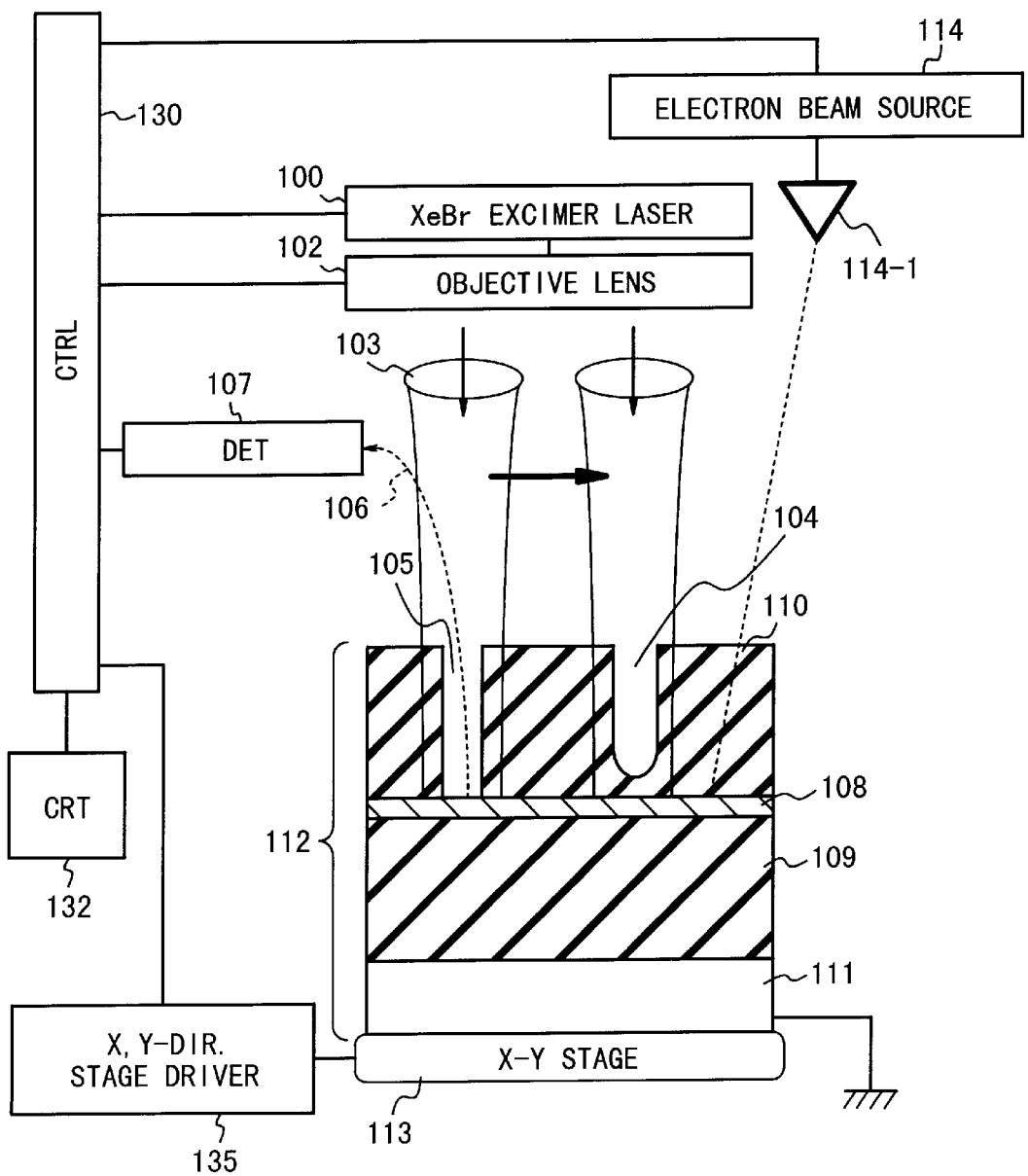
FIG. 4 is a diagram illustrating a testing apparatus for the opening state of a hole according to a third embodiment of the present invention.

Next, a testing apparatus for an opening state of a hole according to a third embodiment of the present invention will be described below with reference to FIG. 4.

The third embodiment is different from the first embodiment in that the laser light scanning system 101 is not mounted. In this case, the laser light itself is not scanned. The XY stage 113 on which the test wafer 112 is placed, is driven by an XY direction stage driver 135 in both of the X-direction and the Y-direction under the control of the controller 130.

In the third embodiment, the optical system is largely simplified, as compared with the first embodiment, because the laser light scanning system 101 is not mounted. The optical system suitable for the ultraviolet laser light is limited to a quartz system optical material in the first embodiment. Since the optical system is expensive, the omission provides a cost reduction merit. Moreover, unlike the objective lens of the telecentric optical system in the first embodiment, the simple objective lens 102 can be used while the optical axis of the laser light is always kept substantially vertical to the test wafer 112 during scanning. Also, since the optical axis is kept vertical as mentioned above, the contrast of the image is enhanced, so that the image becomes clear. The test speed is substantially half that of the first embodiment.

Figure 5:
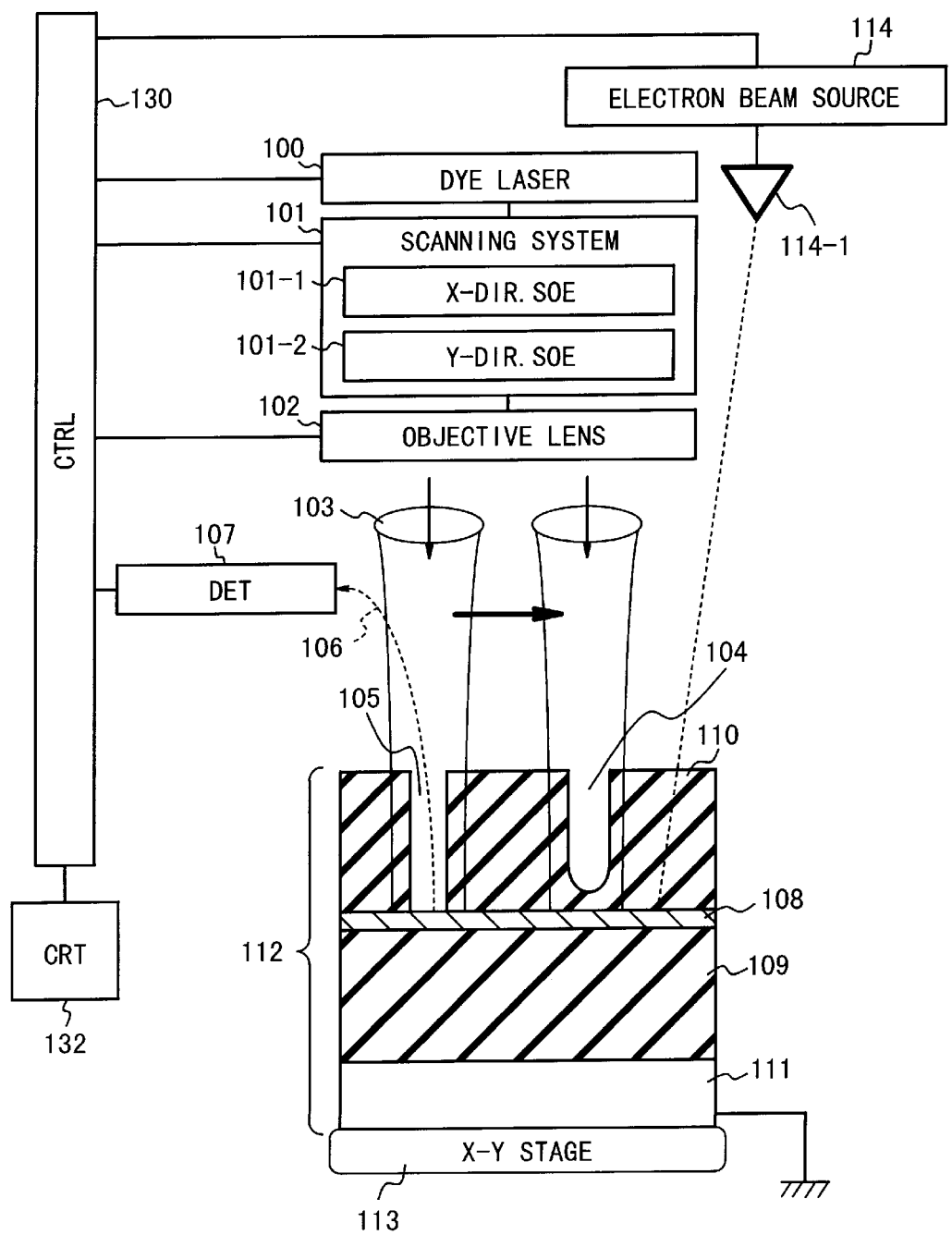
FIG. 5 is a diagram illustrating a testing apparatus for the opening state of a hole according to a fourth embodiment of the present invention.

Next, a testing apparatus for an opening state of a hole according to a fourth embodiment of the present invention will be described below with reference to FIG. 5.

In some of recent processes, the second wiring layer 108 is formed of not a single substance of aluminum but a laminate layer including a thin film of TiN formed on the surface. In the test of a via-hole in such a case, the TiN layer remains such that the aluminum is not exposed, after the etching of the via-hole. In addition, the severely constricted etching condition is required in which there is no remaining film of the intermediate insulating film. As a result, a device for detecting a state in which only the TiN layer is clearly exposed is required.

In view of the above-mentioned circumstances, in the fourth embodiment, a dye laser excited by a YAG laser and having a variable oscillation wave length is used instead of the XeBr excimer laser as the excitation laser light source 100 in the first embodiment. Thus, a laser light beam of 330 nm can be used as a laser light beam slightly shorter than 331 nm corresponding to the TiN work function of 3.75 eV.

If this wave length is used, even when only the aluminum layer is exposed, or even when a second intermediate insulating film 110 remains as the remaining film, the photoelectrons are not emitted because of the work function of the second intermediate insulating film or aluminum layer. Thus, it is possible to detect the state in which the TiN film is kept clear. Conversely speaking, it is possible to find the via-hole in which the TiN film is etched by previously over-etching, or the imperfectly opened via-hole in which the second intermediate insulating film 110 remains as the remaining film by under-etching.

When the test is carried out under the above-mentioned condition, the test speed is identical to that of the first embodiment.

Figure 6:
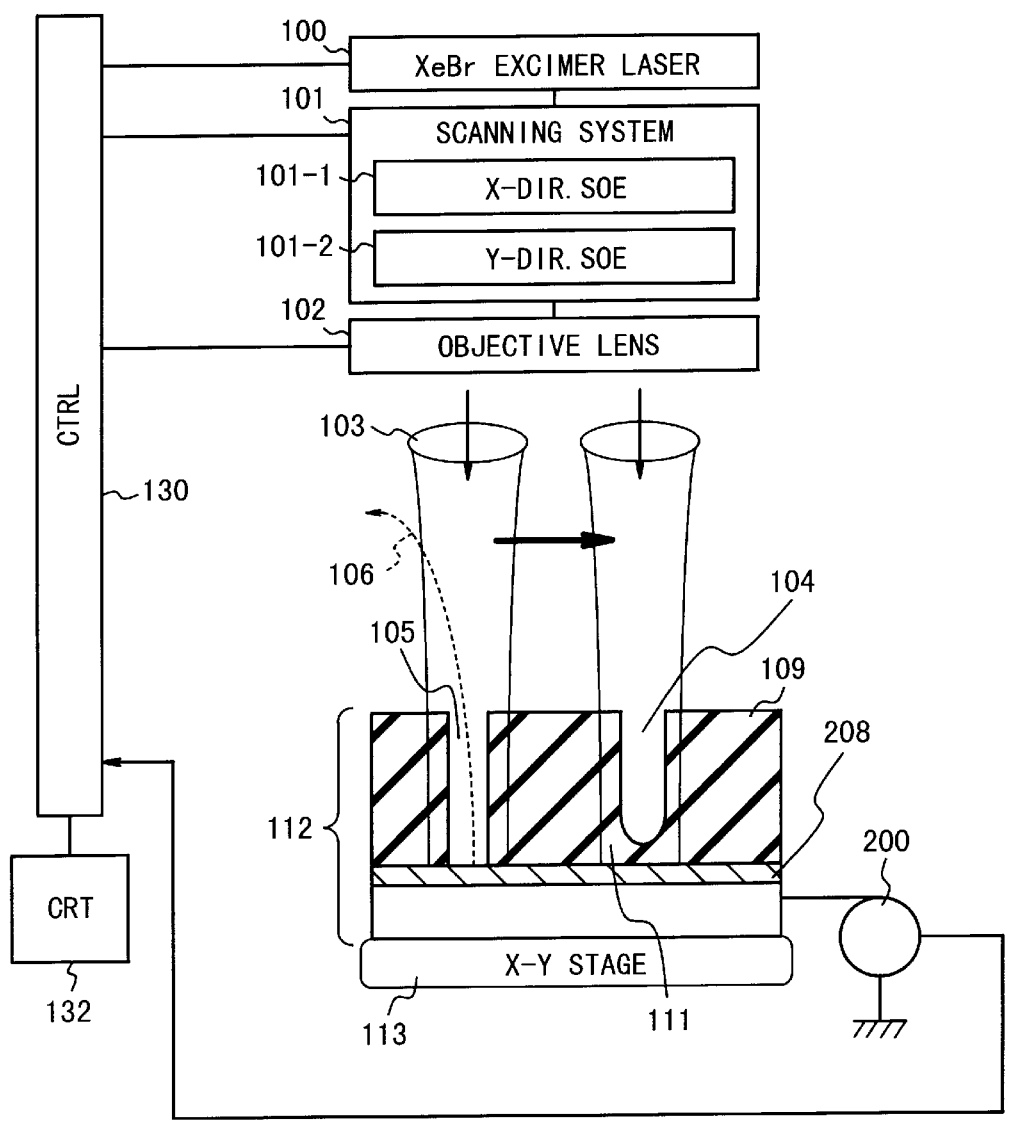
FIG. 6 is a diagram illustrating a testing apparatus for the opening state of a hole according to a fifth embodiment of the present invention.

Next, a testing apparatus for an opening state of a hole according to a fifth embodiment of the present invention will be described below with reference to FIG. 6.

The fifth embodiment is an example of a contact test for a hole referred to as a contact hole. In a semiconductor device on a test wafer 112, a wiring layer 208 is formed on a silicon substrate 111, and an intermediate insulating film 109 is formed on the wiring layer 208. A perfectly opened contact hole 104 and a imperfectly opened contact hole 105 are formed in the intermediate insulating film. In this case, an aspect ratio of the hole is very large, such as 10.

In the fifth embodiment, an ammeter 112 is used instead of the photoelectron detector 107 in the first embodiment. The ammeter 112 is inserted between the test wafer 112 and the ground and has a high sensibility and a fast digital converting function. A lower layer under the bottom of a hole to be tested must be able to be connected to the ground, as a condition that the ammeter 112 can be used. If the hole is the contact hole, the lower layer can be connected to the ground because the silicon substrate 111 serves as the lower layer.

The photoelectrons are emitted at the moment when a laser light 103 is irradiated to the perfectly opened hole 105 of the test wafer 112 satisfying the above-mentioned condition. The wiring layer 208 serving as the lower layer under the hole is transiently positively charged up. Then, a ground current flows so as to neutralize it. This current is detected by the ammeter 200. The controller 130 controls the display 132 to display the detected current value in synchronous with the scanning of the laser light. The current flows through the perfectly opened hole 105, and does not flow through the imperfectly opened hole 104. Hence, this difference can be represented as a contrast image. From this image, it is possible to detect the imperfectly opened hole 104 through which the current does not flow.

As a result of such an test, the test speed becomes identical to that of the first embodiment.

Figure 7:
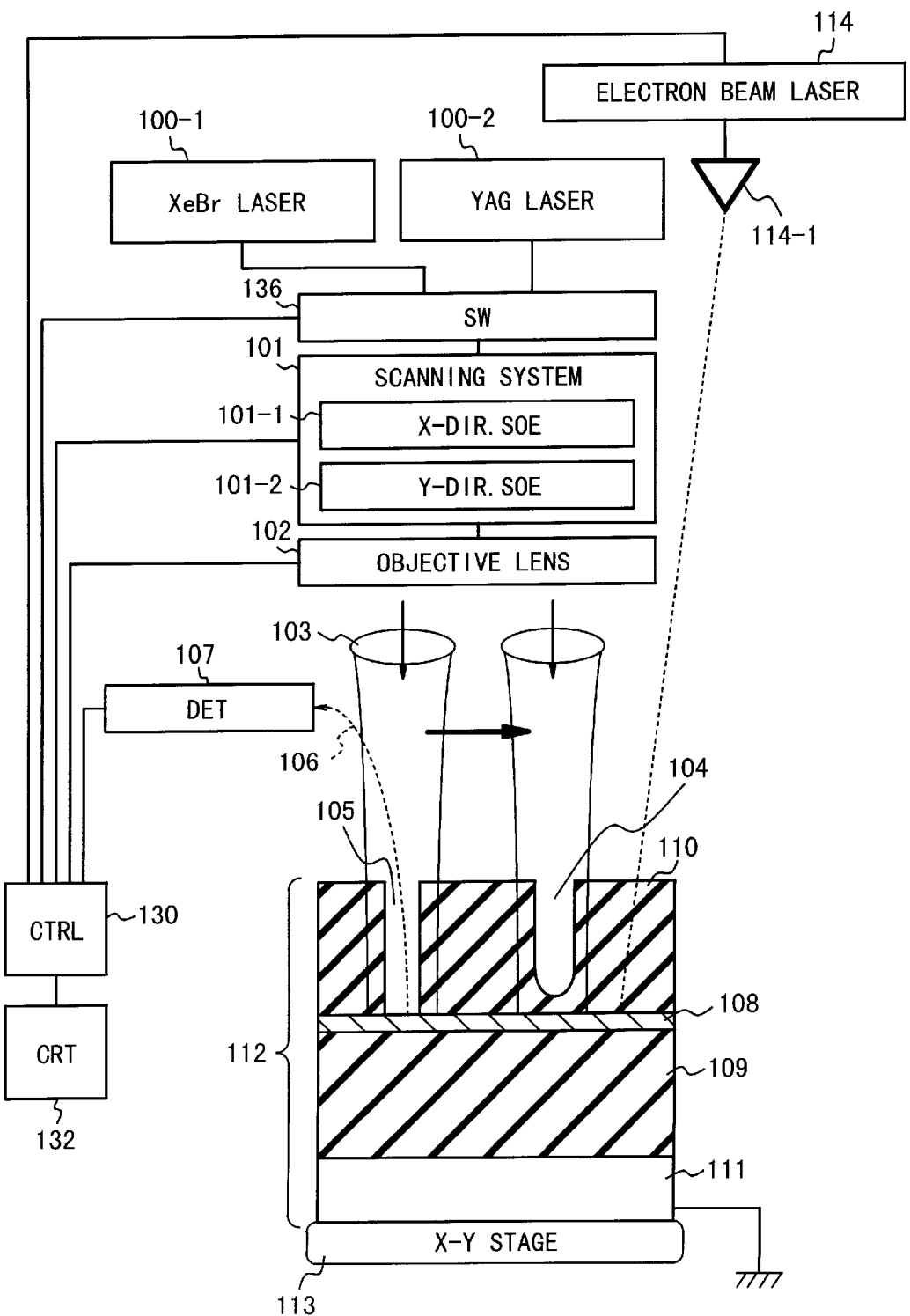
FIG. 7 is a diagram illustrating a testing apparatus for the opening state of a hole according to a sixth embodiment of the present invention.

Next, a testing apparatus for an opening state of a hole according to a sixth embodiment of the present invention will be described below with reference to FIG. 7. In this embodiment, a XeBr excimer laser 100-1 and a YAG laser 100-2 are provided. Which of the laser lights from the XeBr excimer laser 100-1 and the YAG laser 100-2 is incident to a laser light scanning system 101 is determined by an optical switch (SW) 136 controlled by a controller 130.

Even if a hole 105 referred to as a via-hole is perfectly opened by the etching, there may be a case that the surface of a second wiring layer 108 is covered with a natural oxide film and this results in an open defect and a high resistance defect.

If the second wiring layer 108 is made of aluminum, $Al_2O_3$ as its oxide has a work function energy in which an aluminum oxide chemical shift amount of approximate 2.5 eV is added to the aluminum work function of 4.25 eV. That is, $Al_2O_3$ has a work function energy of 6.75 eV. The light having this energy belongs to the region of the X-ray. Hence, the photo-electric effect does not occur by the ultraviolet light.

The XeBr excimer laser is selected by the optical switch 136 similarly to the first embodiment, and used as a laser light source 100. Other settings are similar to those of the first embodiment. Then, the defect is tested. As a result, since the natural oxide film is very thin, the contrast similar to the first embodiment cannot be attained. However, it is possible to detect the imperfectly opened hole 104 covered with an oxide film $Al_2O_3$.

In the case of detecting the imperfectly opened hole 104 with the above-mentioned natural oxide film, if the SEM is used, primary electrons penetrate the oxide film under an acceleration voltage of a radiation electron beam required to observe, since the oxide film is very thin. For this reason, it is difficult to detect the presence or absence of the oxide film. On the contrary, in the present invention, such a difficulty can be avoided to detect the imperfectly opened hole 104.

The testing apparatus according to the present invention detects at a high speed, the many defective contact holes and defective via-holes which have the high aspect ratio of approximate 10 and the small hole diameter of 0.3 micronmeters, even if the holes are covered with the intermediate insulating film and the natural oxide film.

What is claimed is:

1. A testing apparatus for an opening state of a hole in a semiconductor device comprising:
   a laser light radiating system for radiating, to a hole, a laser light having a wave length determined based on a work function of a material of a conductive layer and a work function of a material of an insulating layer, wherein said semiconductor device has said conductive layer and said insulating layer formed on said conductive layer, and said hole is formed in said insulating layer at aim to reach said conductive layer;
   a detector for detecting that photoelectrons are emitted through a portion of said hole to which said laser light is irradiated; and
   a charge supplementing mechanism for supplementing electrons to said conductive layer.

2. A testing apparatus according to claim 1, wherein said wave length of said laser light is a wave length corresponding to an energy in a range in which an outer photo-electric effect is performed to said conductive layer but the outer photo-electric effect is not performed to said insulating layer.

3. A testing apparatus according to claim 1, wherein said laser light is focused on and radiated to a bottom surface of said hole, and it is determined based on the detecting result by said detector whether or not said hole is opened to reach said conductive layer.

4. A testing apparatus according to claim 1, wherein said charge supplementing mechanism includes an electron beam source for sending said electrons to said conductive layer.

5. A testing apparatus according to claim 1, wherein said charge supplementing mechanism is connection of said conductive layer of said semiconductor device to the ground to send the electrons to said conductive layer.

6. A testing apparatus according to claim 4, further comprising a controller for controlling said laser light radiating system and said electron beam source such that said radiation of said laser light and said electron supplement to said conductive layer by said electron beam source are alternately carried out.

7. A testing apparatus according to claim 1, wherein said semiconductor device has a plurality of said holes and a focused beam diameter of said laser light is larger than a diameter of said hole.

8. A testing apparatus according to claim 1, wherein said laser light radiating system has an optically scanning system for scanning said laser light in a two-dimension direction such that said laser light is sequentially radiated to said plurality of holes.

9. A testing apparatus according to claim 1, wherein said laser light radiating system includes:
   an optically scanning system for scanning said laser light in a one-dimension direction such that said laser light is sequentially radiated to a row of said plurality of holes; and
   a driver for scanning said semiconductor device in a direction orthogonal to a scanning direction of said laser light, in response to the scan of said laser light.

10. A testing apparatus according to claim 1, further comprising a driver for scanning said semiconductor device in a two-dimension direction such that said laser light is sequentially radiated to said plurality of holes.

11. A testing apparatus according to claim 1, wherein said detector is a light electron detector.

12. A testing apparatus according to claim 1, wherein said detector is an ammeter connected between said conductive layer and the ground.

13. A testing apparatus according to claim 1, further comprising:

a display; and a display controller for controlling said display such that the detecting result by said detector is displayed on said display with respect to a relative position of said semiconductor device and said laser light.

14. A testing apparatus according to claim 13, wherein said display controller controls said display such that the detecting result by said detector for each of said plurality of holes in said semiconductor device is displayed on said display as a two-dimension contrast image having a brightness distribution proportional to said detection result.

15. A testing apparatus according to claim 4, further comprising alternately performing said radiation of said laser light and said supplement of said electrons to said conductive layer.

16. A method of testing an opening state of a hole in a semiconductor device, comprising the steps of:

radiating to one of a plurality of holes, a laser light pulse having a wave length determined based on a work function of a material of a conductive layer and a work function of a material of an insulating layer, wherein said semiconductor device has said conductive layer and said insulating layer formed on said conductive layer and said plurality of holes are formed in said insulating layer at aim to reach said conductive layer;

detecting that photoelectrons are emitted through said hole in response to said laser light; and supplementing electrons to said conductive layer after said laser light pulse is radiated.

17. A method according to claim 16, wherein said radiating step includes radiating said laser light pulse such that said laser light is focused on and radiated to a bottom surface of said hole, and wherein said detecting step includes determining whether or not said hole is opened to reach said conductive layer, based on the detecting result.

18. A method according to claim 16, wherein said supplementing step includes irradiating electrons to said conductive layer.

19. A method according to claim 16, wherein said supplementing step includes connecting said conductive layer of said semiconductor device to the ground.

20. A method according to claim 16, wherein said wave length of said laser light is a wave length corresponding to an energy in a range in which an outer photo-electric effect is performed to said conductive layer but the outer photo-electric effect is not performed to said insulating layer.

21. A method according to claim 16, wherein said semiconductor device has a plurality of said holes and a focused beam diameter of said laser light is larger than a diameter of said hole.

22. A method according to claim 16, further comprising the step of relatively scanning said semiconductor device and said laser light pulse.

23. A method according to claim 22, wherein said relatively scanning step includes optically scanning said laser light in a two-dimension direction.

24. A method according to claim 22, wherein said relatively scanning step includes:

scanning said laser light in a one-dimension direction; and scanning said semiconductor device in a direction orthogonal to a scanning direction of said laser light.

25. A method according to claim 22, wherein said relatively scanning step includes scanning said semiconductor device in a two-dimension direction.

26. A method according to claim 16, further comprising the step of:

displaying the detecting result of said photoelectrons as a two-dimension contrast image having a brightness distribution proportional to said detection result.

* * * * *

UNITED STATES PATENT AND TRADEMARK OFFICE
CERTIFICATE OF CORRECTION

PATENT NO. : 6,177,681 B1
DATED : January 23, 2001
INVENTOR(S) : Toyokazu Nakamura It is certified that error appears in the above-identified patent and that said Letters Patent is hereby corrected as shown below:

Column 9,
Line 46, after "out" insert -- 10 --

Signed and Sealed this

Twentieth Day of November, 2001

Attest:

NICHOLAS P. GODICI
Attesting Officer  Acting Director of the United States Patent and Trademark Office